United States Patent
Foster et al.

(10) Patent No.: US 7,331,344 B2
(45) Date of Patent: Feb. 19, 2008

(54) BREATHING DEVICE (75) Inventors: Stephen Foster, Uckfield (GB); Stuart Corner, Pevensey (GB); Stephen Harrison, College Green (GB)

(73) Assignees: Electro Medical Equipment Limited, Warwickshire (GB); Frazer-Nash Cobnsultancy Limited, College Green (GB)

( * ) Notice: Subject to any disclaimer, the term of this patent is extended or adjusted under 35 U.S.C. 154(b) by 0 days.

(21) Appl. No.: 10/505,466

(22) PCT Filed: Feb. 21, 2003

(86) PCT No.: PCT/GB03/00758

§ 371 (c)(1),
(2), (4) Date: Mar. 14, 2005

(87) PCT Pub. No.: WO03/070306

PCT Pub. Date: Aug. 28, 2003

(65) Prior Publication Data

US 2005/0150493 A1    Jul. 14, 2005

(30) Foreign Application Priority Data

Feb. 21, 2002 (GB) ................... 0204117.6

(51) Int. Cl.
*A61M 16/00* (2006.01)
(52) U.S. Cl. ............................. 128/204.25; 128/204.18
(58) Field of Classification Search .......... 128/200.24, 128/204.18, 204.24, 204.25, 205.11, 202.27, 128/206.21, 207.18, 206.18, 206.27, 206.11, 128/204.23, 204.21, 200.14, 200.16, 200.18, 128/200.21, 200.22, 203.12, 203.24, 203.28, 128/205.13, 910–912

See application file for complete search history.

(56) References Cited

U.S. PATENT DOCUMENTS

| | | | |
|---|---|---|---|
| 2,985,357 A | | 5/1961 | Carolan |
| 3,630,196 A | | 12/1971 | Bird |
| 3,903,884 A | * | 9/1975 | Huston et al. ......... 128/200.18 |
| 4,098,290 A | | 7/1978 | Glenn |
| 4,151,843 A | * | 5/1979 | Brekke et al. ......... 128/205.25 |
| 4,261,355 A | | 4/1981 | Glazener |
| 4,274,406 A | * | 6/1981 | Bartholomew ......... 128/206.21 |
| 4,282,869 A | | 8/1981 | Zidulka |
| 4,351,328 A | * | 9/1982 | Bodai ...................... 128/202.16 |
| 4,495,946 A | | 1/1985 | Lemer |
| 4,519,388 A | | 5/1985 | Schwanbom et al. |
| 4,537,188 A | * | 8/1985 | Phuc ...................... 128/200.21 |
| 4,681,100 A | | 7/1987 | Brychta et al. |
| 4,796,617 A | | 1/1989 | Matthews et al. |
| 5,000,173 A | | 3/1991 | Zalkin et al. |

(Continued)

FOREIGN PATENT DOCUMENTS

DE    3119814    7/1984

(Continued)

*Primary Examiner*—Teena Mitchell
(74) *Attorney, Agent, or Firm*—Baker & Hostetler LLP (57) ABSTRACT

A breathing device for assisting patients to breath by maintaining positive airway pressure during the breathing cycle comprises a breathing channel in fluid communication with an exhaust channel extending from a junction therebetween. A gas inlet is arranged so as to introduce gas into the breathing channel. A positive pressure may be maintained in the breathing channel wherein the axis of the gas inlet channel is laterally offset at the point at which the gas inlet channel introduces the gas into the breathing channel from the axis of the narrowest part of the breathing channel.

14 Claims, 5 Drawing Sheets

U.S. PATENT DOCUMENTS

| | | | |
|---|---|---|---|
| 5,193,532 A | 3/1993 | Moa et al. | |
| 5,507,282 A * | 4/1996 | Younes | 128/204.21 |
| 5,735,271 A * | 4/1998 | Lorenzen et al. | 128/207.16 |
| 5,975,077 A * | 11/1999 | Hofstetter et al. | 128/204.24 |
| 6,209,539 B1 * | 4/2001 | Loescher et al. | 128/204.18 |
| 6,443,154 B1 * | 9/2002 | Jalde et al. | 128/205.29 |
| 6,612,304 B1 * | 9/2003 | Cise et al. | 128/200.26 |
| 6,745,770 B2 * | 6/2004 | McAuliffe et al. | 128/205.24 |
| 7,047,968 B2 * | 5/2006 | Kniewasser | 128/204.18 |
| 7,152,597 B2 * | 12/2006 | Bathe | 128/202.27 |
| 7,207,332 B1 * | 4/2007 | Lugtigheid | 128/204.28 |

FOREIGN PATENT DOCUMENTS

| | | | |
|---|---|---|---|
| FR | 2506164 | | 11/1982 |
| GB | 2098491 | | 11/1982 |
| JP | 57195466 | | 12/1982 |
| WO | WO 99/24101 | * | 5/1999 |

* cited by examiner

BREATHING DEVICE

CROSS-REFERENCE TO RELATED APPLICATIONS

The present application claims priority to pending Application No. PCT/GB03/00758 entitled BREATHING DEVICE and filed on Feb. 21, 2003, which claims priority to UK Application No. 0204117.6 entitled RESPIRATORY APPARATUS and filed on Feb. 21, 2002, the entire contents of both applications being expressly incorporated by reference herein.

STATEMENT RE: FEDERALLY SPONSORED RESEARCH/DEVELOPMENT (Not Applicable)

BACKGROUND OF THE INVENTION

This invention relates to breathing devices for assisting patients, particularly human patients, to breathe by maintaining a positive airway pressure during the breathing cycle.

It is well recognised that the application of continuous positive airways pressure (CPAP) is a successful clinical technique for assisting patients with breathing difficulties. Recently a particularly successful non-invasive CPAP device has been described in EP-A-0447 443 and marketed by the Applicant as the INFANT FLOW (registered trade mark) generator. This device has been shown to deliver reliable CPAP whilst at the same time resulting in a lower work of breathing when treating respiratory distress syndrome. This lower work of breathing is important as it leads to faster patient recovery times which is of course beneficial to the patient, but which also helps to keep down running costs of intensive care departments.

It has been recognised that the phenomenon of jet bypass, whereby a proportion of fresh gas supplied to the patient passes directly out of the exhaust tube is crucial in giving the low added work of breathing.

BRIEF SUMMARY OF THE INVENTION

The Applicant has realised that, at least for some applications, such devices may be further improved. When viewed from a first aspect therefore the invention provides a breathing device comprising, in fluid communication, a breathing channel and an exhaust channel extending from a junction therebetween; and a gas inlet channel arranged so as in use to introduce gas into said breathing channel such that in use a positive pressure may be maintained in the breathing channel, wherein the axis of said gas inlet channel is laterally offset from the axis of the breathing channel at the point at which the gas inlet channel introduces the gas into the breathing channel.

Thus it will be seen that in accordance with the present invention, a CPAP-type breathing assistance device is provided in which the gas inlet channel is offset from the axis of the breathing channel. It has been found that providing such an offset can reduce the fluctuations in pressure in the breathing channel over the breathing cycle. This is recognised to be beneficial in reducing the work of breathing and thus in aiding patient recovery.

Furthermore, it has been recognised that the amount of lateral offset can be set to give a determinable degree of jet bypass. In particular, the Applicant has recognised that whilst in many cases a constant positive airway pressure is the most appropriate breathing assistance to provide, in some cases it may be desirable to provide an increased pressure during the inhalation phase. This might be appropriate, for example, in particularly serious cases where the patient is unable properly to expand his/her lungs. The increased pressure can assist in the recruitment of alveoli. The increased inhalation pressure may be achieved by setting the degree of bypass appropriately.

Whilst, as set out above, the required bypass effect may be achieved by offsetting the gas inlet from the axis of the breathing tube, it been further recognised that in fact the same effect is achievable by simulating such an offset. Thus, the gas inlet need not be offset from the main axis of the breathing tube if the breathing tube undergoes a change in cross-sectional area and the gas inlet is offset from the central axis of the narrower portion. The narrower portion could be a relatively small proportion of the length of the breathing channel—for example a partial baffle.

When viewed from a more general aspect therefore the present invention provides a breathing device comprising, in fluid communication, a breathing channel and an exhaust channel extending from a junction therebetween; and a gas inlet channel arranged so as in use to introduce gas into said breathing channel such that in use a positive pressure may be maintained in the breathing channel, wherein the axis of said gas inlet channel is laterally offset at the point at which the gas inlet channel introduces the gas into the breathing channel from the axis of the narrowest part of the breathing channel.

Thus it will be appreciated that a preferred embodiment of the aspect of the invention set out above has the breathing channel being of substantially constant cross-sectional area, such that the gas inlet channel is laterally offset from the main axis of the breathing channel.

The breathing channel may have any convenient cross-sectional shape, for example it could be triangular or oval in cross-section. Alternatively it may have a substantially circular cross-section. Similarly the exhaust channel could also have any convenient cross-sectional shape e.g. circular, triangular or oval, and need not be the same shape as the breathing channel.

The gas inlet channel may comprise a discrete tube extending at least partially into the breathing channel. It is preferred however that the gas inlet channel opens into the breathing channel—i.e. that the mouth of the gas inlet is at a wall of the device. Most preferably the gas inlet channel is arranged to open into the junction between the breathing channel and the exhaust channel, on the outer side of said junction.

Preferably the gas inlet channel is laterally offset from the axis of the breathing channel, or the central axis of its narrowest point, in the direction towards the exhaust channel. This means that the jet of fresh gas emerging from the gas inlet channel will be directed at least partially towards the elbow at the inner edge of the junction between the exhaust and breathing channel or to the lower edge of a narrower portion. The elbow or other flow restrictor effectively serves to split the jet of gas between the breathing and exhaust channels, thereby giving the required bypass.

The gas inlet channel could be parallel to the breathing channel. Preferably however it is inclined at a small angle e.g. approximately 5°, to the breathing channel axis in the direction away from the exhaust channel. This has been found to give marginally better performance.

In fact it has been appreciated that the inclination of the gas inlet channel can also have an effect on the degree of bypass, albeit lesser, in general, than the effect of lateral bypass and that a suitably chosen inclination can give a useful degree of bypass, even if the gas inlet channel is not laterally offset. Thus, when viewed from a further aspect the invention provides a breathing device comprising, in fluid communication, a breathing channel and an exhaust channel extending from a junction therebetween; and a gas inlet channel arranged so as in use to introduce gas into said breathing channel such that in use a positive pressure may be maintained in the breathing channel; wherein the axis of said gas inlet channel is inclined relative to the axis of said breathing channel.

As in accordance with the earlier aspects of the invention, the gas inlet channel axis is preferably laterally offset at the point at which it joins the exhaust channel or laterally offset from an axis through the centre of a narrowed section of the breathing channel.

Clearly the degree of lateral offset will affect the relative proportions of the split flows and thus the degree of bypass. Possible embodiments are envisaged in which the offset is in the direction away from the exhaust channel. However such embodiments require a relatively large inclination of the gas inlet channel which is undesirable for other reasons.

As has been explained above, both the offset and the inclination of the gas inlet channel relative to the breathing channel, or narrowest part thereof, influence the degree of bypass achieved during use. This, in turn, has varying beneficial effects on the pressure profile in the breathing channel. In general a particular pressure profile will be suitable for a large number of patients. However the Applicant has recognised that in some circumstances it may be desirable to be able to change the pressure profile by changing the degree of bypass. In some preferred embodiments therefore the breathing device comprises two or more gas inlet channels at different offsets and/or inclinations. A physician may then decide which gas inlet to use for the desired mode of operation.

Additionally or alternatively, in some embodiments a movable gas inlet channel is provided. It is envisaged that the inlet channel may be moved so either the inclination of the offset may be varied, or indeed it may be possible to vary both. In one example the gas inlet channel could be pivotably mounted to the rest of the device with a flexible gaiter or the like being provided to ensure a gas-tight seal. In another example the gas inlet could be slidably mounted to the rest of the device. Again a suitable seal or gasket may be provided.

In accordance with all aspects of the invention, it is preferred that the gas inlet channel has a smaller cross-sectional area than either the exhaust or breathing channels, preferably less than a quarter of either. In one particular embodiment in which the channels are circular, the ratio of their diameters is 1.4 mm to 5 mm.

Preferably the breathing and exhaust channels are substantially linear and most preferably meet substantially at a right angle or greater.

The breathing device of the invention may be adapted to be attached directly to the face of a patient. For example it may comprise a pair of nasal prongs for insertion into the patient's nose. Indeed where the breathing device is adapted for use by infants, the infant's nostrils will effectively form part of the breathing tube. Alternatively, the device may comprise or be adapted to be connected to a mask for fitting over a patient's face—e.g over the nose and mouth, the mask being in communication with the breathing channel.

In some preferred embodiments an elongate tube is provided in fluid communication with the exhaust channel. This is not essential to the operation of the device but it has been found to reduce the noise generated.

BRIEF DESCRIPTION OF THE SEVERAL VIEWS OF THE DRAWINGS

Certain preferred embodiments of the present invention will now be described, by way of example only, with reference to the accompanying drawings in which.

DETAILED DESCRIPTION OF THE INVENTION

Figure 1:
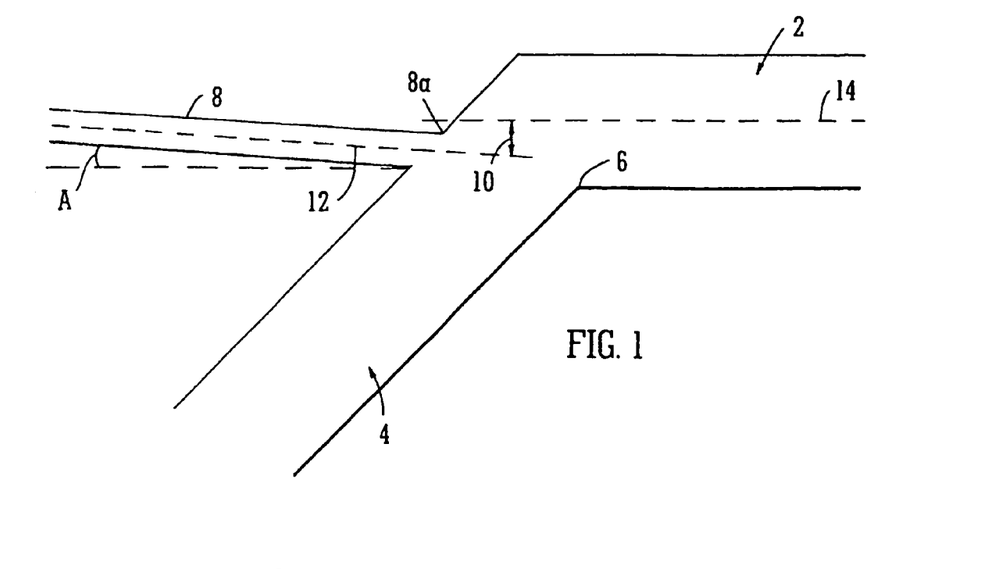
FIG. 1 is a schematic cross-sectional view of a breathing device in accordance with the invention.

The breathing device of FIG. 1 generally comprises a breathing channel 2 and an exhaust channel 4 in fluid communication with one another. The breathing channel 2 is provided at its distal end with a face mask, nasal prongs or other suitable device (not shown) as the patient interface.

The exhaust channel 4 is continued by a tube (not shown) which is open to the atmosphere. It joins the breathing channel 2 at an oblique angle to form a corner 6 on the inside of the junction.

A gas inlet channel 8 joins the device so as to introduce gas into the breathing channel 2 in the region of its junction with the exhaust channel 4. It will be seen that at the point 8a at which the gas inlet channel 8 introduces the gas, there is an offset 10 between the axis 12 of the gas inlet channel 8 and the axis 14 of the breathing channel 2.

The respective axes 12, 14 of the gas inlet channel 8 and the breathing channel 2 are not quite parallel since the former axis 12 is inclined at an angle A. Furthermore, it may be seen that the diameter and therefore cross-sectional area of the gas inlet channel 8 is substantially smaller than that of the breathing or exhaust channels 2, 4.

Figure 2A:
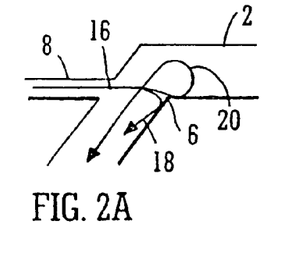
FIGS. 2a to 2c are respective schematic flow diagrams showing air flow in the device during the breathing cycle.
Figure 2B:
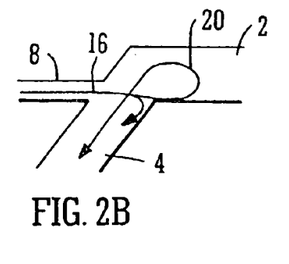
Figure 2C:
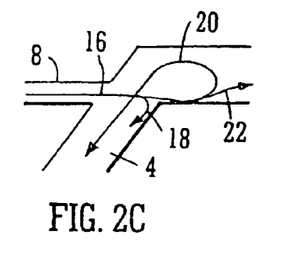

FIGS. 2a to 2c show, schematically, operation of the device shown in FIG. 1. Firstly FIG. 2a shows the pattern of fresh gas flow during patient exhalation. As a result of the offset 10 between the axes 12, 14 of the gas inlet and breathing channels (see FIG. 1) the jet 16 of fresh gas from the gas inlet channel 8 impinges upon the corner 6 at the junction of the breathing and exhaust channels 2, 4. This causes part of the jet 18 to "bypass" the breathing channel 2 to flow straight down the exhaust channel 4. The degree of bypass is enhanced by the remainder of the jet 20 which loops back on itself in the breathing channel 2 and also passes down the exhaust channel 4. This flow 20 combines with the gas being exhaled by the patient to deflect the jet 16 downwardly and so causes more high momentum gas to impinge upon the corner 6.

The effect of the bypass is to reduce pressure in the breathing channel 2 and so the work required by the patient to exhale, as compared to what it would have been otherwise without bypass.

FIG. 2b shows the pattern of fresh gas flow at zero breath (the transition between patient exhalation and inhalation). It will be seen that the bypass portion of the jet 18 is significantly reduced since the jet 16 is no longer being deflected by the exhaled air. However the offset 10 and the looped-back fresh gas flow 20 mean that there is still some bypass. It may further be observed that the loop 20 of fresh gas is larger than during the exhalation phase shown in FIG. 2a since the fresh gas is no longer working against the pressure of the air being exhaled and because less of it is being bypassed.

Finally, FIG. 2c shows the pattern of fresh gas flow during patient inhalation. In this phase the degree of bypass is similarly low, but still not completely absent, as the low pressure created inside the patient's lungs draws in the majority 22 of the fresh gas flow. As shown there is still a portion 20 of the fresh gas which loops back on itself and passes down the exhaust channel 4. Depending upon the needs of the patient, the looped flow may in fact be reversed to supplement the fresh gas with ambient air.

Figure 3:
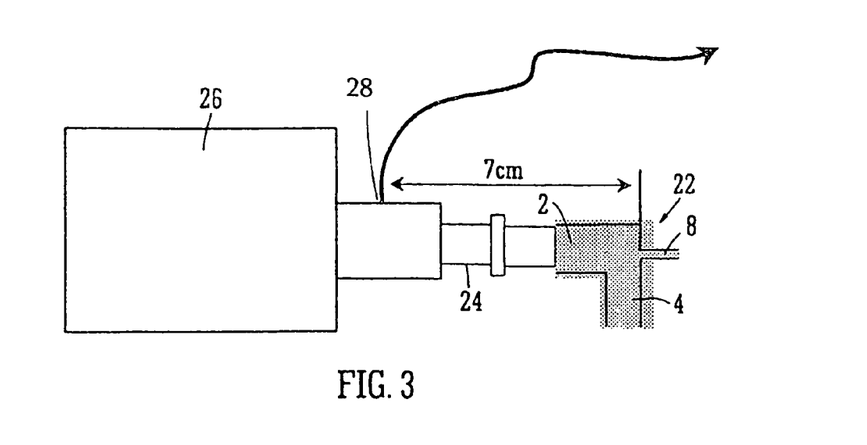
FIG. 3 is a schematic diagram of a test set-up used to test an embodiment of the invention.

FIG. 3 shows schematically an experimental set-up used to test a breathing generator 22 in accordance with the invention. The breathing generator 22 had a breathing channel 2 and an exhaust channel 4 at right angles to one another. Both channels had an internal diameter of 5 mm. A gas inlet channel 8 with a 1.4 mm internal diameter was provided at the end of the breathing channel such that its central axis is offset by 1.5 mm relative to the axis of the breathing channel.

The breathing channel 2 was connected by means of a tube 24 to a lung simulator 26 comprising a piston driven by an actuator (not shown). The actuator is controlled by a computer in order to simulate a representative patient breathing profile. At the inlet to the lung simulator 26 a pressure feed 28 was taken to a pressure transducer connected to a personal computer (not shown) to allow the pressure to be measured and recorded. This pressure feed was taken 7 cm downstream of the end of the gas inlet channel 8.

Figure 4:
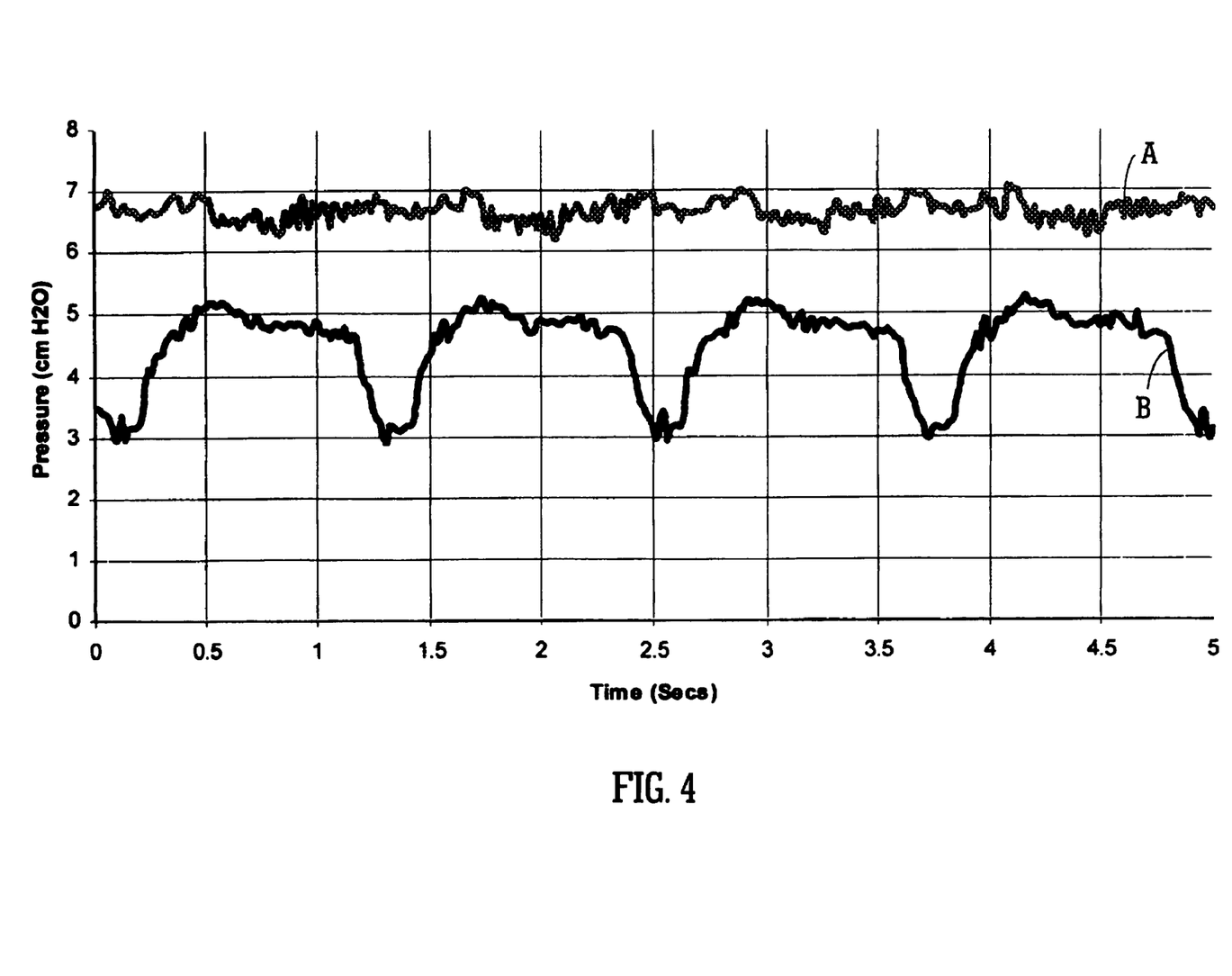
FIG. 4 is a graph of pressure v time for an embodiment of the invention and for a prior art device tested under the same conditions for the purposes of comparison only.

The artificial lung was set to a tidal volume of 30 millilitres and an inhale to exhale ratio of 3:7, which are reasonably typical figures for an infant. The gas inlet channel 8 was then connected to a source of fresh gas at 37° C. (so called "medical air") For the first experiment, the rate of fresh gas flow was set to eight litres per minute. The pressure recorded by the pressure transducer is shown by line A on the graph in FIG. 4.

The experiment was then repeated with a known breathing device—the Applicant's INFANT FLOW (registered trade mark) generator under the same conditions (except that pressure was measured at the generator pressure connection, which accounts for only approximately 0.25 cm $H_2O$ pressure difference) with a fresh gas flow rate of eight litres per minute. The results may be seen from the line B in FIG. 4. It is clear from this not only that a higher airway pressure is achievable for a given flow rate, but also that the pressure fluctuation over the breathing cycle has been even further reduced in accordance with the present invention.

Figure 5:
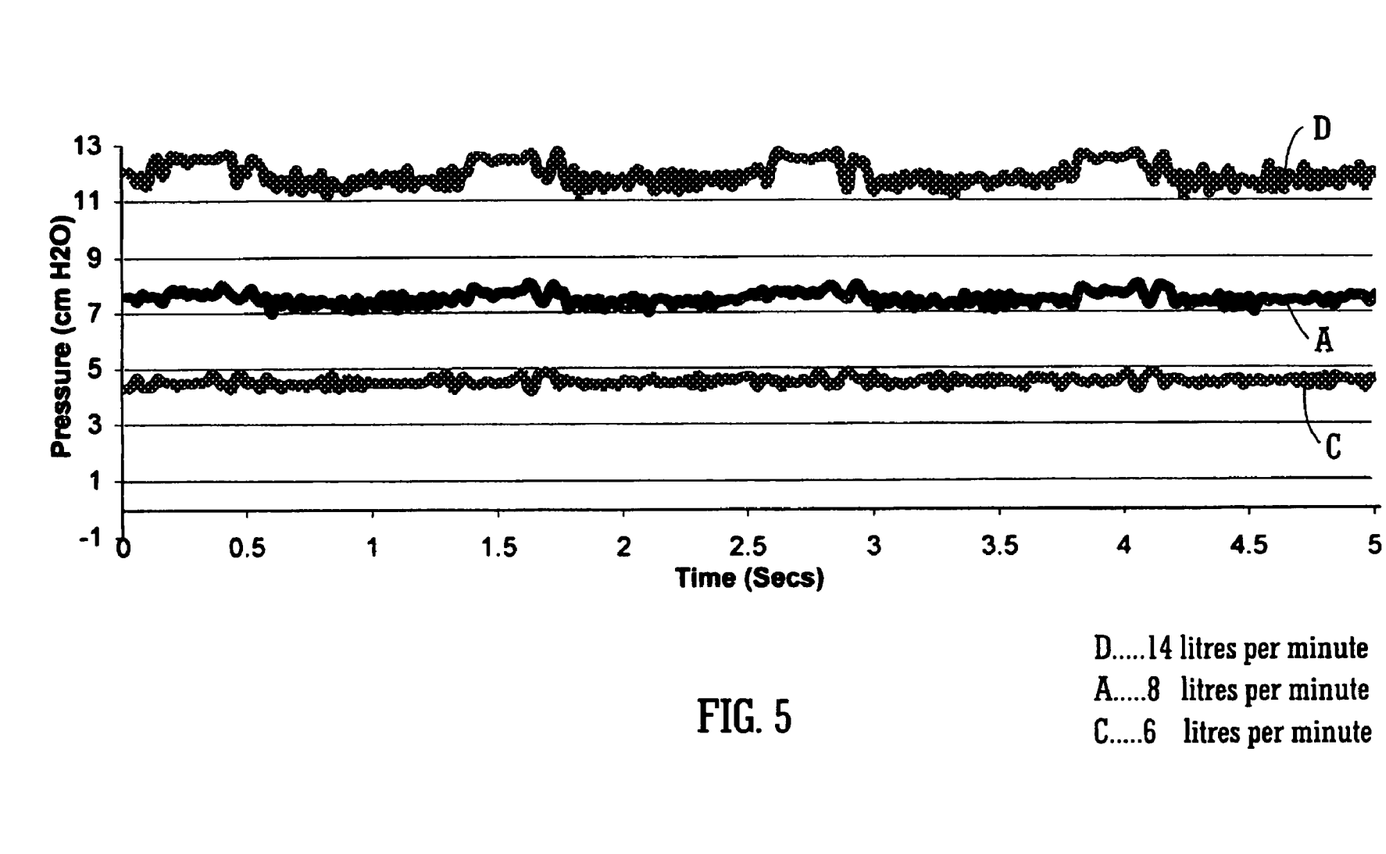
FIG. 5 is a graph of pressure v time for three different gas inlet pressures.

The experiment was repeated with fresh gas flows of six and fourteen litres per minute and results are shown by lines C and D respectively in FIG. 5. FIG. 5 also shows the results obtained with a flow rate of eight litres per minute (line A). As may be seen, at six and eight litres per minute (lines C and A respectively) there is negligible pressure fluctuation. At fourteen litres per minute (line D), there is in fact negative fluctuation—in other words there is an increase in pressure on inhale and a decrease on exhale. This gives a degree of breathing assistance and is potentially extremely beneficial for those patients having difficulty breathing.

Thus it will be seen that at least an embodiment of the invention provides a breathing device with very low fluctuations in pressure which is therefore able to assist in breathing with minimal added work of breathing as compared to already beneficial prior art devices.

Figure 6:
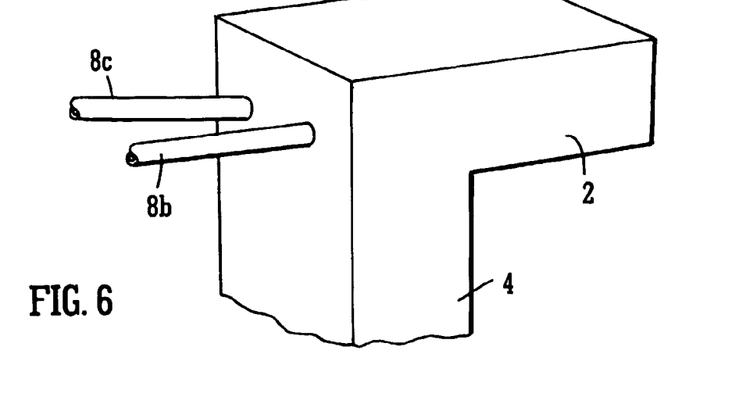
FIGS. 6 to 8 are respective schematic perspective views of further embodiments of the invention.

A further potential embodiment of the invention is shown schematically in FIG. 6. In this embodiment, two separate gas inlet channels 8b and 8c are provided. The first inlet 8b is provided offset below the axis of the breathing channel 2 to provide a predetermined degree of offset. The second inlet 8c has the same amount of offset but is also inclined with respect to the axis of the breathing channel 2. This will give a higher degree of bypass which may be required in certain situations—e.g. if a higher fresh gas flow is required. In use a physician or medical attendant may select which inlet channel 8b, 8c to use as needed. This could simply be by placing a gas supply tube over the desired inlet channel or it could be by means of a two-way valve.

Figure 7:
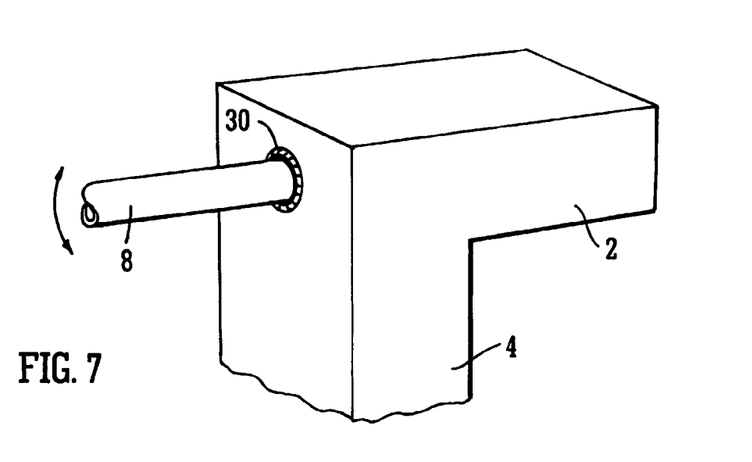

Another potential embodiment is shown in FIG. 7. In this embodiment the gas inlet channel 8 is shown extending through a rubber gaiter 30. Inside the breathing device (not shown) the gas inlet channel 8 is pivotally attached to the main body. This allows it to be inclined up and down to provide the desired degree of bypass. A screw or the like could be provided to hold the inlet 8 in the desired inclination.

Figure 8:
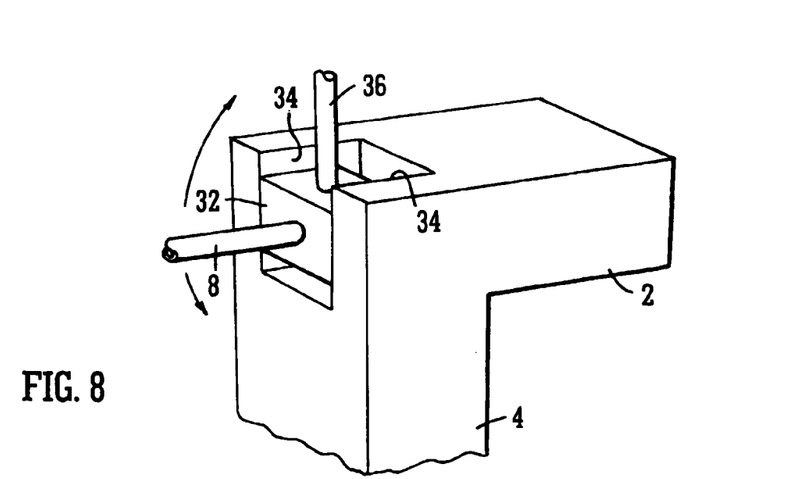

FIG. 8 shows another possible embodiment. In this embodiment the gas inlet channel 8 is connected to a block 32 received in a recess 34 in the corner of the device. The gas inlet channel is in gaseous communication with an internal passage in the block which opens into the interior of the device to provide fresh gas into the breathing channel. The block 32 is a reasonably gas-tight fit into the side walls of the recess 34. Stops may be provided to limit the movement of the block 34. It will be seen that the block 34 is provided on its upper face with a protrusion 36 to facilitate movement thereof.

A further embodiment of the breathing device is shown in FIGS. 9a to 9e. In this embodiment the breathing channel 2 is of a substantially triangular cross-section as shown by the end elevations 9c and 9d. The breathing channel 2 and an exhaust channel 4 are in fluid communication with one another. As before, a gas inlet channel 8 joins the device so as to introduce gas into the breathing channel 2 in the region of its junction with the exhaust channel 4. As in previous embodiments, it will be seen that at the point 8a at which the gas inlet channel 8 introduces the gas, there is an offset 10 between the axis 12 of the gas inlet channel 8 and the axis 14 of the breathing channel 2.

Figures 9A, 9C, 9D:
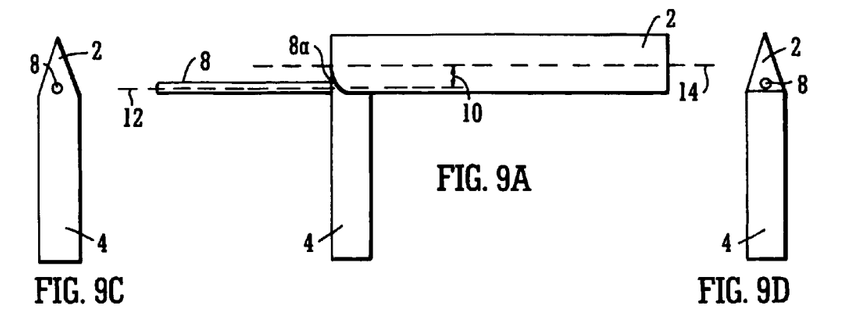
FIGS. 9a to 9e are various elevations of another embodiment of the breathing device in accordance with the invention.
Figure 9B:
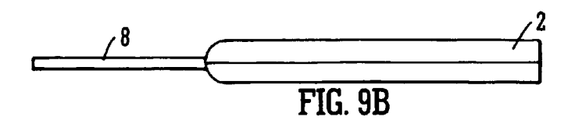
Figure 9E:
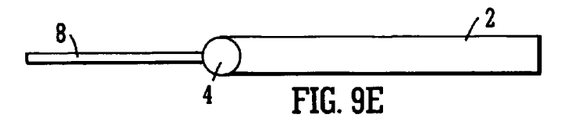

Unlike previously however, the side elevation, FIG. 9a, shows that the breathing channel 4 is at a right angle to the exhaust channel 4. The exhaust channel 4 is of substantially circular cross section, as shown in the bottom view of the device given in FIG. 9e, and is therefore not the same cross section shape as that of the breathing channel 2.

Figures 10A, 10C, 10D:
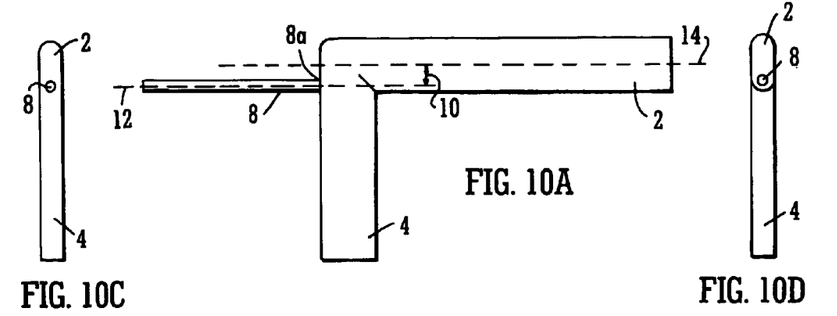
FIGS. 10a to 10e are various elevations of a further embodiment of the breathing device in accordance with the invention.
Figure 10B:
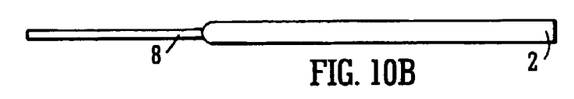
Figure 10E:
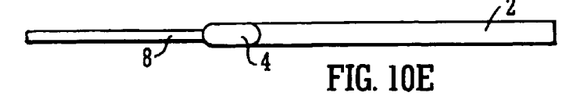

Finally, FIGS. 10a to 10e show another embodiment of the breathing device. In this embodiment the breathing channel 2 is of a substantially oval cross-section as shown by the end elevations 10c and 10d. Again, the side elevation, FIG. 10a, shows that the breathing channel 4 is at a right angle to the exhaust channel 4. The exhaust channel 4 has substantially oval cross-section and therefore has the same cross-sectional shape as the breathing channel 2, as shown in the bottom elevation of the device given in FIG. 10e.

It will be appreciated by those skilled in the art that many variations and modifications of the described embodiments are possible within the scope of the present invention. For example, the breathing device may be configured deliberately to increase the airway pressure during the inhalation phase by increasing the offset between the axes of the gas inlet channel and the breathing channel in order to give a corresponding smaller degree of bypass. Such a device could be useful for treating acute respiratory distress syndrome in which the increased pressure on inhalation can help in the recruitment of alveoli.

Furthermore, the breathing channel need not be of constant bore as depicted. It may comprise a local reduction in the cross-sectional area—e.g. by virtue of a baffle, step or other protrusion. In this case the gas inlet channel may not be offset from the main axis of the breathing channel but will be offset from the effective central fluid axis thereof which is determined by the reduction in cross-section or bore.

The invention claimed is:

1. A breathing device comprising, in fluid communication, a breathing channel and an exhaust channel extending from a junction therebetween; and a gas inlet channel arranged so as in use to introduce gas into said breathing channel such that in use a positive pressure may be maintained in the breathing channel, wherein an axis of the gas inlet channel is laterally offset from an axis of the breathing channel at the point at which the gas inlet channel introduces the gas into the breathing channel, wherein the gas inlet channel is arranged to open into the junction between the breathing channel and the exhaust channel on an outer side of the junction, wherein the axis of the gas inlet channel is laterally offset from an axis of the breathing channel at a narrowest part of the breathing channel.

2. The device of claim 1 wherein the breathing channel is of a substantially constant cross-sectional area.

3. The device of claim 1 wherein the breathing channel has a substantially circular cross-section.

4. The device of claim 1 wherein the gas inlet channel opens into the breathing channel.

5. The device of claim 1 wherein the gas inlet channel is laterally offset from the axis of the breathing channel in a direction toward the exhaust channel.

6. The device of claim 1 wherein the gas inlet channel is inclined relative to the breathing channel axis.

7. The device of claim 1 comprising at least two gas inlet channels at different lateral offsets and inclinations.

8. The device of claim 1 wherein the gas inlet channel is narrower than at least one of the exhaust and breathing channels.

9. The device of claim 1 wherein the breathing and exhaust channels are substantially linear and intersect one another at an angle of at least about ninety degrees.

10. The device of claim 1 wherein the breathing device is adapted to be attached directly to a face of a patient.

11. The device of claim 1 wherein the breathing device is adapted to be connected to a mask.

12. The device of claim 1 wherein the gas inlet channel is arranged to provide a degree of gas bypass such that increased pressure is provided during inhalation.

13. The device of claim 1 wherein the gas inlet channel has a cross sectional area that is smaller than a cross sectional area of at least one of the breathing and exhaust channels.

14. A breathing device comprising, in fluid communication, a breathing channel and an exhaust channel extending from a junction therebetween; and a gas inlet channel arranged so as in use to introduce gas into said breathing channel such that in use a positive pressure may be maintained in the breathing channel, wherein an axis of the gas inlet channel is laterally offset from an axis of the breathing channel at the point at which the gas inlet channel introduces the gas into the breathing channel, wherein the gas inlet channel is arranged to open into the junction between the breathing channel and the exhaust channel on an outer side of the junction, wherein the breathing device further comprises a movable gas inlet channel.

* * * * *